US005574052A

United States Patent [19]
Rose et al.

[11] Patent Number: 5,574,052
[45] Date of Patent: *Nov. 12, 1996

[54] AGONIST-ANTAGONIST COMBINATION TO REDUCE THE USE OF NICOTINE AND OTHER DRUGS

[75] Inventors: Jed E. Rose, Venice; Edward D. Levin, Los Angeles, both of Calif.

[73] Assignee: Robert J. Schaap, Los Angeles, Calif.; a part interest

[*] Notice: The term of this patent shall not extend beyond the expiration date of Pat. No. 5,316,759.

[21] Appl. No.: 235,454

[22] Filed: Apr. 29, 1994

Related U.S. Application Data

[63] Continuation of Ser. No. 54,144, Apr. 30, 1993, which is a continuation of Ser. No. 855,868, Mar. 23, 1992, Pat. No. 5,316,759, which is a continuation of Ser. No. 231,092, Aug. 11, 1988, abandoned, which is a continuation-in-part of Ser. No. 840,072, Mar. 17, 1986, Pat. No. 4,846,199.

[51] Int. Cl.$^6$ .......................... A61K 31/44; A61K 31/465
[52] U.S. Cl. .......................... 514/343; 424/10; 514/660; 514/810; 514/812; 514/813; 514/922; 514/947; 131/270; 131/271; 131/329
[58] Field of Search .............................. 424/10; 514/660, 514/810, 812, 813, 922, 947, 343; 131/270, 271, 329

[56] References Cited

U.S. PATENT DOCUMENTS

| | | | |
|---|---|---|---|
| 2,981,641 | 4/1961 | O'Neill | 131/17 |
| 3,071,509 | 1/1963 | O'Neill | 514/343 |
| 3,980,766 | 9/1976 | Shaw et al. | 424/10 |
| 4,597,901 | 7/1986 | Etscorn | 514/813 |
| 4,783,456 | 11/1988 | Glassman | 514/214 |
| 4,803,208 | 2/1989 | Pasternak | 514/282 |
| 4,846,199 | 7/1989 | Rose | 131/329 |
| 4,935,429 | 6/1990 | Dacks et al. | 514/288 |
| 5,075,341 | 12/1991 | Mendelson et al. | 514/282 |
| 5,189,064 | 2/1993 | Blum et al. | 514/561 |
| 5,219,858 | 6/1993 | Parnell | 514/264 |
| 5,256,669 | 10/1993 | Askanaz et al. | 514/282 |
| 5,266,574 | 11/1993 | Zagan et al. | 514/282 |
| 5,316,759 | 5/1994 | Rose et al. | 424/10 |

OTHER PUBLICATIONS

Comparitive Toxicity For Mice . . . , P. Driscoll. Praeventimedizin 17 (4), 211–213.
Changes In Body Temperature . . . , G. H. Hall, Br. Jr. of Pharmacology (1972) 44, 634–641.
Temperature Responses In The Rat . . . , J. Baird et al, European Jr. of Pharmacology 21 (1973) 203–211.
Cardiovascular Responses . . . , British Jr. (1973) 47, 196–205. M. J. Larry et al.
Effects Of Nicotine On Self–Stimulation Pradhan, et al., Jr. of Pharmacology and Experimental Therapeutics 1971, vol. 176, No. 1.
Titration of Oral nicotine Intake . . . , S. D. Glick, et al. Nature, vol. 233, Sep. 17, 1971, 207–208.

Nicotine Self–Administration . . . , H. M. Hanson, et al., Ch. 7 Norman A. Krasnegor, NIDA Research Monograph 23, Jan. 1979.
Influencing Cigarette Smoking . . . , I. P. Stolerman, et. al., Psychopharmacologia (Berl.) 28–247–249 (1973).
Effects of Mecamylamine On Human Cigarette Smoking . . . , Nemeth–Coslett, et al., Pharmacology (1986) 88:420–425.
Rapid Phsiologic Effects of Nicotine . . . , J. Henningfield, et al., U.S. Dept. of Health and Human Services, 259–265.
Could Nicotine Antagonists Be Used . . . , by I. P. Stolerman, Br. Jr. of Addiction (1986) 81, 47–53.
Mecamylamine Pretreatment . . . , C. S. Pomerleau, et. al., Pharmacology (1987) 91:391–393.
Clinical Evaluation of Mecamylamine . . . , F. S. Tennant, Jr., et al., NIDA Research Monograph, Feb. 9 (1984). 239–246.
Withdrawl From Nicotine Dependence . . . , F. S. Tennant, Jr., et al., NIDA Research Monograph, 55 (1985).
Double–Blind Comparison . . . , F. S. Tennant, Jr., UCLA, Los Angeles, California.
Involvement of Cholinergic Nicotine–like Receptors . . . Kurt Anderson, et al 1982 Acta Physicl Scand, 11G(1), 41–50.
Behavioral Effects of Intraventricularly Administered Nicotine . . . Victor J. DeNoble, et al., Psychopharmacologia, (Berlin) 77(4), 317–21, 1982.
Nicotine–catecholaminergic Interactions in Rat Brain: . . . Kevin A. Roth, et al., Journal of Pharmacology EXP. THET, 221(2), 416–20, 1982.

(List continued on next page.)

Primary Examiner—Herbert J. Lilling
Attorney, Agent, or Firm—Robert J. Schaap

[57] ABSTRACT

A method of treating and reducing a drug dependency such as a nicotine dependency is provided. The method comprises initially administering to a subject a drug, such as nicotine or another agonist of the drug in an amount which would normally provide the desired pharmacologic effects and at least partially satiate the needs for the drug by a user. The method also comprises administering to the subject an antagonist to the drug or its other agonist in an amount sufficient to at least partially block the pharmacologic effects of the drug or its other agonist while there is a substantial amount of the drug or other agonist present in the system of the user. In one embodiment of the invention, the drug and the antagonist are administered substantially simultaneously so as to occupy a substantial portion of the receptors of the user for that drug thereby blocking or attenuating the effects of any further intake of the drug or other agonist. In another embodiment, the drug or its other agonist is first administered and the antagonist is self–administered by a subject in a manner which mimics the use of the drug thereby counter-conditioning the drug user to the stimuli associated with the normal administration of the drug. The invention further provides a method of therapeutically treating psychophysiologic diseases and disorders involving neuronal dysregulation. The method additionally provides a pharmacologic composition for the treatment and reduction of drug dependence.

41 Claims, 2 Drawing Sheets

OTHER PUBLICATIONS

Cardivascular Response in Central Administration of Cholinergic Drugs . . . In Ho Kim, 1981, Ulhakpu Nonmunzip, 34(4) 669–79.

Interanimal Olfactory Ques in Operant Drug Discrimination Procedures. K. Extanoc, et al., Psychopharmacology (Berlin) 1981, 73(4), 363–71.

Suppressive Effects of Intraperitoneal and Intraventricular Injections . . . Robert J. Waldbillig Pharmacology, Biochemical Behavior, 12(4), 619–23.

Nicotine–like Behavioral Effect After Small Doses of Mecamylamine P. Driscoll, Psychopharmacologia, 46(1), 119–21 (1976).

Gawin, FH. Chronic Neuropharmacology of Cocaine: Jr. of Clin. Psychiatry, 49:2 (Feb. 1988), pp. 11–16.

Goeders, NE et al. Cortical Dopaminergic Involvement *Science,* 221 (Aug. 1983) pp. 773–775.

Harris, LS. Central Neurohunoral Systems, *Fed Proceed.,* 20:1 (Jan.–Feb. 1970), pp. 28–32.

Harris, L. et al: Protection Againts Disipropyfluorophosphate Intoxic Arch. of Pharm. Spring 1984 327:64–69.

Krystal J., et al. The Intermittent Antagonist Paradigm: *Problems of Drug Depend.* 1989, p. 45.

Judson, BA, et al. Uses of Naxoxone, *Research On The Treatment . . . Of The Art.* 1983, Chap. 1. pp. 1–3.

Meyer, RE, et al. A Behavioral Paradigm, Arch. of General Psych., 33 (Mar. 1976) pp. 371–377.

Rose, J. E., et al, "Pharm Biochem. & Behavior," vol. 41, #1, Jan. 1992, pp. 219–226.

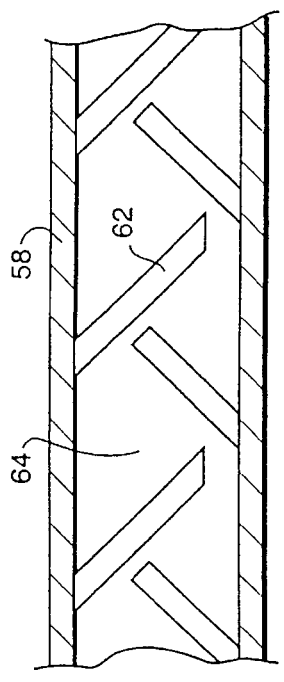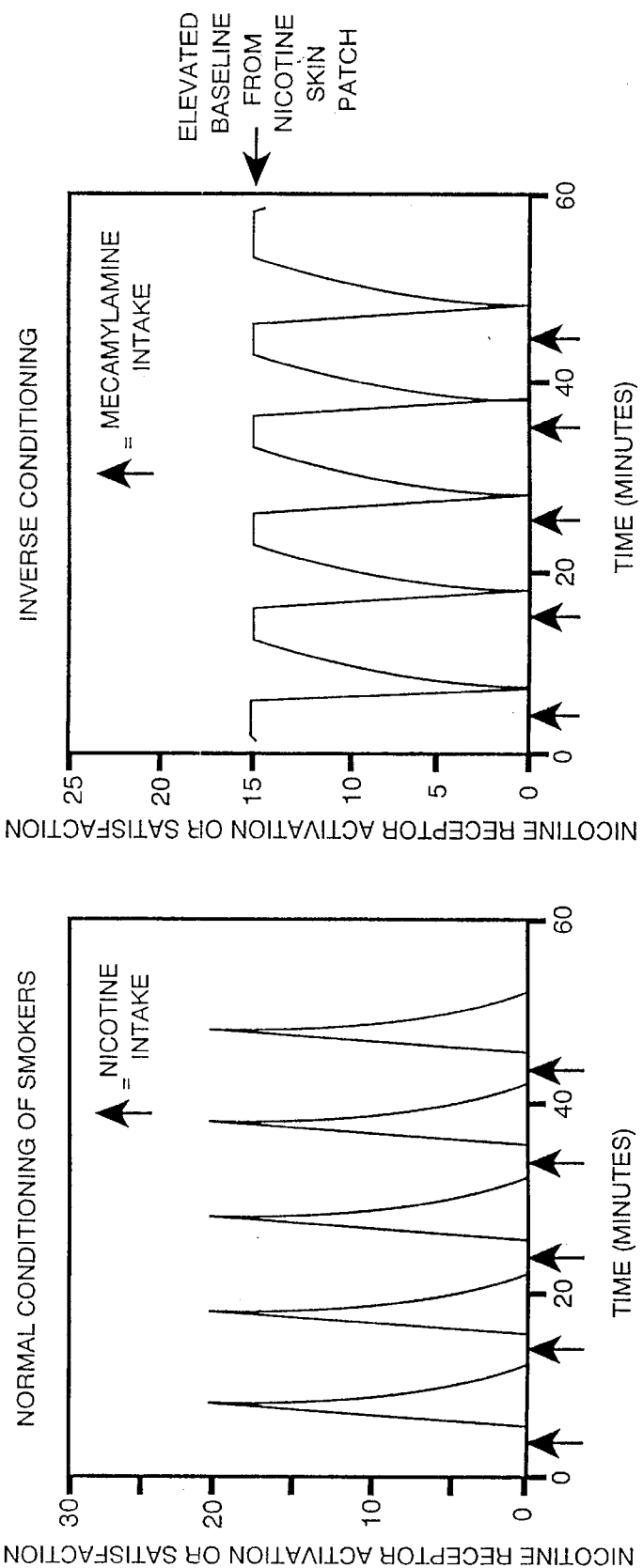

AGONIST-ANTAGONIST COMBINATION TO REDUCE THE USE OF NICOTINE AND OTHER DRUGS

RELATED APPLICATION

This application is a continuation of a co-pending patent application Ser. No. 054,144, filed Apr. 30, 1993 for "Agonist-Antagonist Combination To Reduce The Use Of Nicotine And Other Drugs" which is a continuation of our patent application Ser. No. 855,868, filed Mar. 23, 1992 for "Agonist-Antagonist Combination To Reduce The Use Of Nicotine And Other Drugs", now U.S. Pat. No. 5,316,759 which is a continuation of our patent application Ser. No. 231,092, filed Aug. 11, 1988 for "Agonist-Antagonist Combination To Reduce The Use Of Nicotine And Other Drugs", (now abandoned) which is a continuation-in-part of patent application Ser. No. 840,072, filed Mar. 17, 1986, entitled "Smoking of Regenerated Tobacco Smoke" (now U.S. Pat. No. 4,846,199, dated Jul. 11, 1989).

BACKGROUND OF THE INVENTION

1. Field of the Invention

This invention relates in general to certain new and useful improvements in methods and compositions for treating and reducing drug dependency and for therapeutically treating psychophysiologic diseases and disorders involving neuronal dysregulation and more particularly, to methods and compositions of the type stated which rely upon the administration of a combination of a drug or another agonist and an antagonist to the drug.

2. Government Rights

This invention was made with the support of the Veterans Administration of the United States government. The government has certain rights in this invention.

3. Brief Description of the Prior Art

The substantial use of drugs and particularly, the widespread abuse of drugs has led to increased incidence of health problems and has even largely contributed to significant increases in crime. It has been well established that the intake of the drug nicotine through tobacco smoking has resulted in various adverse health conditions. While the use of drugs, such as nicotine, do not necessarily lead to increased incidence of crime, use of this drug and similar related drugs does present significant health problems.

While the use of other addictive drugs including controlled substances such as various narcotics, e.g., heroin and cocaine, also can result in adverse health conditions, these more serious drug uses have a significant social impact in that they give rise to a substantial increase in numerous types of criminal activity. Various governmental agencies have expended substantial sums of money in attempting to eradicate or at least reduce the incidence of crime, but without much success. Accordingly, in recent years, there has been an increased emphasis on attempting to treat and reduce drug dependency.

The use of drugs is also involved in the treatment of various psychophysiologic disorders, and particularly psychiatric disorders involving dysregulation of a neurotransmitter. In addition, certain diseases involving imbalances of the autonomic nervous system are treated by administration of certain drugs. Here again, these drugs may have serious side effects in that while they may attenuate a certain disorder, they exacerbate other disorders. Further, many of the drugs used to treat these disorders can produce dependence as for example a dependence on diazepam (Valium). Therefore, the subject, while finding some release from the disorder or disease, may become severely addicted to the drug which is used.

In general, two approaches have been used in the pharmacologic treatment of drug dependence. The first approach is often described as the "substitution approach" and provides an alternative drug which is designed to theoretically allow the user to withdraw from the habitually abused drug without suffering the aversive symptoms normally associated with a withdrawal from a drug. As a simple example, methadone is often administered to heroin addicts in the treatment of heroin addiction. It was anticipated and initially believed that a substitution of methadone for heroin, for example, would lead to the eventual cessation of all drug use after a weaning period in which the dose of the substituted drug was gradually reduced.

This first approach to drug dependency has met a very low rate of success. It has been found that the substitution of one drug for another does not typically wean the subjects from all drugs. In fact, it has been found in many cases that the drug users will store the substituted drug, such as the methadone, and continue to use the more addictive drug, heroin or morphine, and only use the stored substitute, methadone, when the heroin or morphine is not readily available. Thus, this first approach to reduced drug dependency has met with very little success.

There have also been various proposed treatments for the administration of nicotine (the putative addictive substance in tobacco smoking) as a replacement for tobacco smoking. One of the most successful approaches which have been used to date in reducing the incidence of tobacco smoking relies upon nicotine containing chewing gum. The use of this type of gum suffers from several problems, including not only the bad taste and destruction of dental appliances, but the gastrointestinal upset which results therefrom and which also reduces compliance. Moreover, the nicotine containing chewing gums do not satisfy that craving which most smokers experience for the distinct sensations in the throat and chest elicited by the nicotine in smoke. Over the course of many years of tobacco smoking, these particular sensations have become an important part of and conditioned with the habit of smoking and help maintain tobacco smoke dependency.

There have also been several proposals for administering nicotine through various aerosol sprays. However, the aerosol sprays are designed to supply that amount of nicotine which would have been acquired by a user through the normal channel of tobacco smoking. The sprays result in severe respiratory tract irritation. There is no available means to provide the nicotine either by means of an oral or nasal spray and attenuate the severe irritating effects of the nicotine.

The second known general approach which has been used in the pharmacologic treatment of drug dependence involves the blocking of the reinforcing effects of the abused drug. It is theorized that by reducing the motivation of the user, there would be a reduced incidence of self-administration of a drug by the user. As a simple example, naltrexone is presently used to block the reinforcing effects of heroin and mecamylamine has been used to block the reinforcing effects of nicotine. This latter approach has not been found to be effective in that the intense withdrawal symptoms suffered by the user encourage compensating use of the addictive drug and thereby reduce compliance with the treatment unless a sufficient period of abstinence has elapsed so that the individual's nervous system is accustomed to the absence of the abused drug. The administration of an antagonist alone also creates a dysphoric state which encourages relapse and return to the abused drug.

Each of the aforementioned approaches have only been used experimentally. Moreover the individual antagonist approach and the individual agonist approach have each been found to be relatively ineffective. The second approach has been ineffective due to the fact that there are significant withdrawal or other adverse symptoms. This causes the drug abuser to return to his original drug habit in order to avoid the pain and discomfort associated with the withdrawal. Thus, this latter approach to reduce drug dependency has also met with little success.

Heretofore, no one has attempted to combine the sustained administration of a drug agonist and an antagonist to that drug in a therapeutic treatment. It would appear that the administration of an agonist and its antagonist would accomplish little, since the antagonist would effectively cancel out the effects of the agonist with a result that the combination would be equivalent to giving nothing at all.

OBJECTS OF THE INVENTION

It is, therefore, one of the primary objects of the present invention to provide a method of reducing the dependency on drugs by utilizing a combination of an agonist and an antagonist.

It is another object of the present invention to provide a method of the type stated for reducing drug dependency by simultaneously administering a drug or another agonist of that drug along with an antagonist to that drug and thereby occupy a substantial number of the receptors of a subject available to that drug or its agonist.

It is a further object of the present invention to provide a method of the type stated which enables administering an agonist and antagonist without causing an over-activity or under-activity of the receptor for the agonist thereby avoiding dangerous side effects which would occur if the agonist or antagonist were given alone in the same dosages.

It is a another salient object of the present invention to provide a method of the type stated in which a drug or another agonist of that drug is administered to an individual to provide a certain systemic level and an antagonist is self-administered by the individual which causes a reduction in the satisfaction associated with the intake of the drug or its other agonist.

It is also an object of the present invention to provide a method for treating psychophysiologic disorders and diseases involving neuronal dysregulation by the simultaneous application of an agonist and an antagonist in relative amounts so that substantial portions are present in the bloodstream in the patient having the disorder or disease.

It is an additional object of the present invention to provide a novel composition of a drug or another agonist of that drug and an antagonist to that drug.

With the above and other objects in view, our invention resides in the novel features of form and arrangement and combination of steps in the method and in the components forming part of the composition as hereinafter described.

BRIEF SUMMARY OF THE INVENTION

The present invention relates in general terms to a method of treating and reducing drug dependency. Any of a number of known drug dependencies can be treated in accordance with the method of the invention including for example, dependency on nicotine, heroin (or morphine) cocaine benzodiazepines, and the like. The invention in a broad aspect relies upon a combination of an administration of a drug or another agonist of the drug and an antagonist to the drug. The present invention also provides a unique method of therapeutically treating psychophysiologic diseases and disorders involving neuronal dysregulation by a simultaneous administration of a drug or another agonist of the drug and an antagonist to the drug.

The term "agonist" is used in a broad sense and includes the drug of interest. Thus, for example, in this case, nicotine is an agonist and heroin is an agonist. Methadone is merely another agonist for heroin since it provides effects similar to that of heroin. Thus the term "agonist" as used herein, unless otherwise specified, will include the drug itself.

The method in a broad sense, comprises initially administering to a subject a drug or another agonist of this drug in an amount which would normally provide the desired pharmacologic effects. Moreover, the amount of the drug applied would at least partially satiate the needs for the drug by the user. The method also involves the administering to a subject an antagonist to the drug or its other agonist in an amount sufficient to at least partially block the pharmacologic effects of the drug or its other agonist while there is a substantial systemic amount of the drug or its agonist present.

The method of the present invention involves two general approaches to the treatment of drug dependency and to the therapeutic treatment of the above described psychophysiologic diseases and disorders which involve use of drugs. In the first approach, there is a treatment for the dependency on the drug by saturating a substantial portion of the known receptors for that drug with a combination of the drug or its other agonist and an antagonist to that drug or such other agonist. In this case, the agonist or drug is administered in an amount to which the subject is generally dependent upon that drug to thereby satisfy a demand for the drug. The antagonist is generally simultaneously administered to the same subject in an amount to attenuate the pharmacologic effects of the drug or its other agonist. In this case, the drug or its other agonist and the antagonist are preferably present in such an amount that more receptors of the drug are occupied by the drug and the antagonist than could safely be occupied by the drug alone or the antagonist alone. Moreover, a lesser number of the receptors are left available to respond to the drug thereby insulating the user from the reinforcing effects of the drug and at the same time minimizing adverse symptoms associated with the antagonist.

In this case, the purpose of the invention is to saturate the receptors of the drug to thereby insulate the individual from the reinforcing effects of the drug. In the case of nicotine, the individual would be administered both nicotine and an antagonist to nicotine, such as mecamylamine. In the case of other drugs such as heroin, or its agonist, methadone, the antagonist naltrexone would be administered.

In accordance with this aspect of the invention, the drug may be present in an amount which would otherwise be toxic in the absence of the antagonist but the toxicity is offset by the presence of the antagonist. The drug should preferably be administered in a sufficiently high dose to occupy a sufficient number of the receptors and thereby substantially reduce a subject's demand for the drug.

In one preferred embodiment, both the drug, or its other agonist, and the antagonist may be administered by means of a transdermal patch, as hereinafter described in more detail. The drug or its other agonist and for that matter the antagonist, may be administered by other means such as oral administration, intravenous administration etc. In order to wean the person from the use of the drug, both the drug, or its other agonist, and the antagonist may be reduced in selected amounts over a period of time.

The use of this approach is effective in that the user will receive little or no satisfaction from taking additional amounts of the drug inasmuch as a very substantial portion of the receptors for that drug are already occupied by the initial dose of the drug and the initial dose of the antagonist to the drug.

The second general approach used in the administration of the agonist and an antagonist involves an inverse conditioning to the stimuli associated with the taking of the abused drug. In this case, the method involves the administering to a subject a drug or another agonist of the drug in an amount which would achieve a systemic level of the drug to which the subject was previously accustomed. This approach to the method also involves the self-administration of an antagonist to the drug or its other agonist, but only at selected intervals. Moreover, the antagonist is preferably administered in a form similar to the administration of the abused drug, as hereinafter described.

While this approach does increase the saturation of the receptors for the drug by the presence of the drug and the antagonist, it more importantly causes a reduction of the enjoyable effects associated with the taking of the drug. The subject is administered a certain amount of the drug or other agonist to provide a desired systemic level. The administration of the antagonist is preferably in a form with sensory cues which mimics or closely simulates the form in which the user was accustomed to taking the drug, as aforesaid. Thus, by taking the drug in this form, there is an inverse conditioning or counter-conditioning of the stimuli associated with the taking of the drug.

As a simple example of this latter approach in treating and reducing drug dependency, the dependency on nicotine could be reduced by providing a desired systemic level of the nicotine through a transdermal patch or other means. The antagonist, such as mecamylamine, could be incorporated into a smoking device, such as a simulated cigarette which provides many if not most of the sensory cues in normal tobacco smoking. In this way, when the user took a puff from the simulated cigarette, instead of receiving nicotine, he would receive an antagonist, namely the mecamylamine, thereby further depriving the user of the pharmacologic effects of nicotine to which he or she was previously accustomed. The usual conditioning is that smoking is associated with increased nicotine stimulation and pleasurable effects. However, in this case, smoking and its attendant sensory cues would be associated with decreased nicotine stimulation and the unpleasant effects of withdrawal whenever the user smoked.

It can be observed that one important factor in each of the above identified approaches to the method of the present invention is that there is generally a sustained level of the agonist in a user's bloodstream. When using the first approach, there would generally be a sustained level of both the agonist and the antagonist since they are generally simultaneously administered. In the second approach, there would at least be the sustained level of the agonist and the user would self-administer the antagonist at the will of the user. Thus, there would be peaks in the amount of the antagonist in the bloodstream of the user of the second approach.

Preferably, in both approaches to the method of the invention, the agonist is administered by a route which is different than that employed in the actual use of the drug. Thus, in the case of nicotine, administration of an agonist would occur by means of a transdermal patch or a route other than by way of smoking. In the case of the heroin, methadone would likely be used because it has a longer acting effect than heroin, but would be administered by a route different than the user employed for the administration of heroin. Thus, if the user self-administered heroin through a hypodermic needle, the methodone would be administered orally or by means other than a hypodermic needle. In this way, there will not be any reinforcement of the original response obtained by the common method of using the drug.

In both approaches, it can also be observed that there is essentially no self-administration of the agonist alone. In other words, the agonist may be self-administered in combination with the antagonist as for example, a composition in the form of a pill or tablet. Otherwise, the agonist would generally always be administered in a therapy, as for example, in a treatment center, or the like. The antagonist could be self-administered, as described above.

The present invention is also highly effective in the treatment of various psychophysiologic disorders and diseases involving neuronal dysfunction, as described above. The invention utilizing both the agonist and the antagonist is effective in treating disorders involving dysregulation of a neurotransmitter as for example, in manic depression and schizophrenia. Imbalances of the autonomic nervous system can also be treated by the concurrent agonist-antagonist administration, as well. In particular, sympathetic nervous system disorders e.g. hypertension could also be treated by this approach with the adrenergic agonist-antagonist combinations.

The present invention also provides a unique composition of both an agonist and an antagonist. The composition is novel and unobvious in view of the fact that one would not normally attempt to combine an agonist and an antagonist for the reasons described above. Moreover, it is important to have a single composition which may be in tablet or pill form, for example, or which may be administered through a transdermal patch. In this way, the user who is typically an abuser of a drug or another agonist of that drug will not be able to separate the desired portion of the composition, namely the drug or agonist from the antagonist. When the user takes the composition, the user will receive both the drug or its other agonist and the antagonist to the drug.

This invention possesses many other advantages and has other purposes which will be made more clearly apparent from a consideration of the forms in which it may be embodied. They will now be described in more detail for purposes of illustrating the general principles of the invention, but it is to be understood that such detailed description is not to be taken in a limiting sense.

BRIEF DESCRIPTION OF THE DRAWINGS

Figure 1:
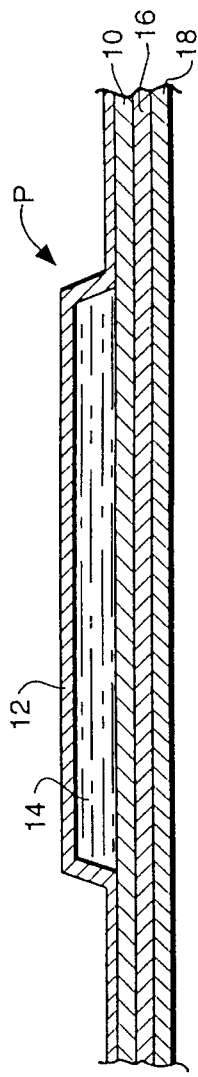
Figure 2:
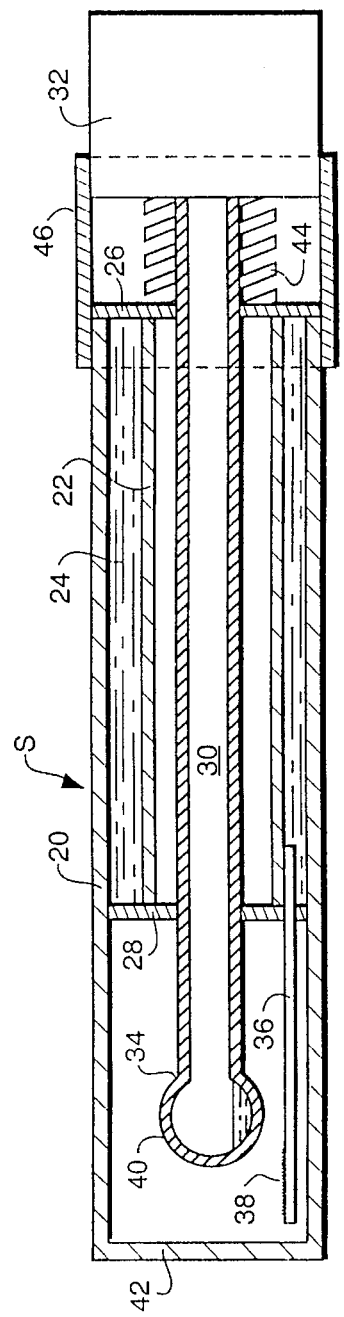
Figure 3:
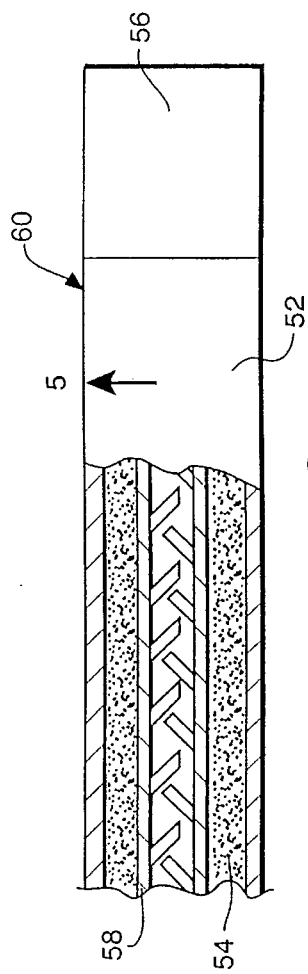
Figure 4:
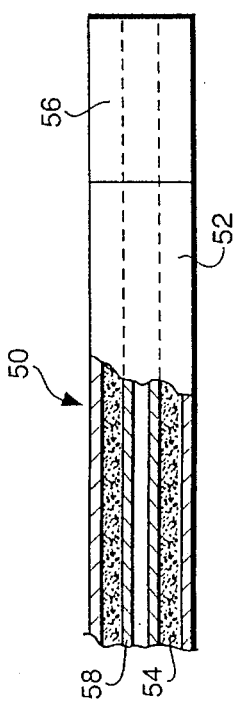

Having thus described the invention in general terms, reference will now be made to the accompanying drawings (two sheets) in which:

FIG. 1 is a somewhat schematic vertical sectional view of a transdermal patch for the transdermal administration of an agonist or an antagonist;

FIG. 2 is a vertical sectional view of an apparatus capable of being used for inhaling an aerosol of an agonist or an antagonist;

FIG. 3 is a schematic side elevational view, partially broken away and in section, and showing a modified form of apparatus for inhaling an aerosol of an agonist or an antagonist;

FIG. 4 is a schematic side elevational view, partially broken away and in section, and showing another modified form of apparatus for inhaling an aerosol of an agonist or an antagonist;

FIG. 5 is a fragmentary sectional view taken along line 5—5 of FIG. 4;

FIG. 6 is a graph showing a normal conditioning of a smoker with nicotine receptor activation as a function of time; and FIG. 7 is a graph showing an inverse conditioning of smokers with nicotine receptor activation as a function of time.

DETAILED DESCRIPTION OF PREFERRED EMBODIMENTS

Referring now in more detail and by reference characters to the drawings, which illustrate several practical embodiments of the present invention, the invention relies in its principle aspect, upon the administration of a drug, or another agonist of the drug, and an antagonist to the drug, as previously described. As also indicated above, there are two major approaches to reduction of drug dependency using a combination of the agonist and an antagonist.

In the first of these approaches, an effective treatment strategy is based upon the combined administration of the agonist and an antagonist. The net result of the administration of the drug, or another agonist of that drug and its own antagonist is that even more receptors of the users brain for that drug are occupied than if either the agonist or the antagonist were given alone. As a result, the drug user is further insulated from any reinforcing effects of the abused substances. As an example, by administering a dose of nicotine and dose of mecamylamine, the user is insulated from the formerly desirable effects associated with the smoking of tobacco and which desired effects were primarly the obtaining of nicotine. Few receptors are left available to respond to the abused substance in this case because the receptor system is at least partially saturated.

It should be understood that the receptor system could only be partially saturated in that there could be serious adverse consequences to the patient or other subject if all of the receptors were occupied by either a drug or an agonist. Nevertheless, in the context of the present invention, a much larger number of receptors are occupied than would otherwise be occupied if the subject was receiving only a drug or other agonist and the antagonist.

A further advantage of this approach over the administration of an agonist alone, or an antagonist alone, is that the toxic effects of either drug are offset by the other. As a simple example, in the case of nicotine, it may not be safe to administer a sufficiently high dose of the nicotine to occupy enough receptors for obtaining a maximal suppression of an individual's craving for cigarettes. However, by concurrently administering an antagonist for the nicotine, such as mecamylamine, a higher dose of the nicotine could be administered. In like manner, it is possible to deliver a higher dose of a highly addictive drug, such as heroin or morphine, when naltrexone is administered.

The agonist and the antagonist are preferably simultaneously administered to the subject. However, it should be understood that the antagonist could be administered shortly after the administration of the agonist or otherwise, the agonist could be administered shortly after the administration of the antagonist. It is important, however, in the context of this mode of treatment that there is a generally similar therapeutic amount of the antagonist along with the agonist. In this way, the user will not suffer a severe withdrawal symptom which would otherwise occur with the presense of a large amount of the antagonist and a very small amount of the agonist. In like manner, the user will not be able to obtain the pharmacologic effects to which he or she was normally accustomed if there is not an excess of the agonist without a corresponding presence of a substantial amount of the antagonist.

Any means for delivering the agonist and the antagonist may be employed. For example, the agonist and the antagonist may be administered by means of a transdermal patch, as hereinafter described or it may be administered by means of a pill or tablet, or the like. Moreover, the agonist and an antagonist could be administered intravenously or by other means known for administration of medicaments e.g. sublingually, etc.

The preferred modes of administering the agonist or the antagonist and preferably both relies upon the use of a transdermal patch P of the type illustrated in FIG. 1 of the drawings. This patch P is adapted for application to a suitable portion of a smoker's body, as for example, on a forearm or a chest of the individual or the like.

The patch P comprises a lower liquid permeable membrane or layer 10 along with a suitable non-permeable covering or outer enclosing layer 12 and which forms a reservoir 14 therebetween. This reservoir 14 is sized to receive an agonist or an antagonist or both and which usually may be provided in a liquid form. The layer 10 may be provided on its under surface with an adhesive layer 16 covered by a releasable backing 18. Thus, when the releasable backing 18 is removed, the patch P can be adhered to the skin of a user through the adhesive layer 16. The adhesive layer 16 is also sufficiently porous so that any agonist or antagonist contained within the reservoir 14 may be transdermally applied to the user. In like manner, and for this purpose, small apertures could be formed within the adhesive layer 16, if desired.

The membrane 10 and the outer enclosing layer 12 may be formed of a cotton material or similar cloth-like material which is capable of retaining, but yet permitting dispensing of the agonist and antagonist or a liquid carrier which would hold the agonist and the antagonist. For this purpose, both the agonist and the antagonist may be liquid, or otherwise dissolved in a liquid carrier. The patch P may also be provided in the reservoir 14 with a silicone polymer matrix comprised of a cross-linked rubber and having micro-sealed compartments which are effectively formed by the cross-linking of the silicone rubber.

The exact details of construction of the patch P are not critical with respect to the present invention and other forms of dermally applicable patches can be used. One such patch is illustrated, for example, in U.S. Pat. No. 3,797,494 to Zaffaroni. Other patches which can be used are illustrated in U.S. Pat. No. 3,731,683 to Zaffaroni and U.S. Pat. No. 4,336,243 to Sanvordeker et al.

The patch P preferably has a size of about two centimeters by two centimeters at a minimum. Preferably, the patch has a surface area of about five centimeters by five centimeters with a thickness of about two to three millimeters. There is no effective outer limit on the size of the patch, except for convenience. When administering nicotine as the drug, the nicotine may be present in an amount so as to provide that amount of nicotine which would be acquired by a smoker. As a simple example, a patch could deliver a few milligrams of nicotine per hour. For a 24-hour delivery period the patch would have a size and thickness to retain about a minimum of 50 milligrams of nicotine.

In one of the preferred embodiments, when utilizing a transdermal patch, nicotine should be available so as to provide one to four milligrams per hour. The smoker normally obtains about two to about four milligrams per hour of nicotine as a result of a normal smoking pattern. Thus, at least the amount of nicotine to which the smoker is accustomed is generally present. The mecamylamine is present in an amount of 0.5 milligrams to about one milligram per hour delivery. These relative amounts of the nicotine and the mecamylamine are present at the start of any nicotine reduction program and may be reduced after a period of time. After a period of time, the nicotine is reduced to no more than one milligram of nicotine to be delivered per hour along with about 0.5 milligrams of mecamylamine.

The patch has been found to be highly effective in that it provides a steady rate of delivery of both the agonist and the antagonist. In this way, there are no excessive levels of either, as previously described. Oral time release capsules can also provide the same effect. However, better control is provided when using the transdermal patch. An oral spray such as an aerosol spray can be used to administer the nicotine and the mecamylamine or for that matter, the other agonists and antagonists. However, the delivery of nicotine through an oral spray could present a problem due to the harshness and the severe irritation which results in the respiratory tract when inhaled, although this may be mitigated by mecamylamine.

The patch described herein can be placed on any convenient area of the users skin, such as, the underside of the forearm of the user's body or on the chest of an individual. In this way, when the patch is applied to the user's body it will release a continuous supply of nicotine to the smoker.

The nicotine and/or the mecamylamine may be dissolved in an inert vehicle, such as, for example, K-Y jelly or any other liquid carrier which does not react with the body or with the nicotine or the other agonists and the mecamylamine and other antagonists. The vehicle must also readily permit transdermal migration of the nicotine and mecamylamine. One of the primary liquid carriers which may be used is water. However, various low molecular weight alcohols, such as ethanol, etc. could be used. In addition, glycerol, propylene glycol, petrolatum, etc. are effective carriers for the nicotine and mecamylamine.

The nicotine and mecamylamine are each added to the liquid carrier in an amount of about 3 percent by weight to about 10 percent by weight, particularly when water is the liquid carrier. In this case the amount of the two components added to the carrier are limited by the solubility of the mecamylamine. The amount of nicotine and mecamylamine to be added to the carrier is a function primarily of the desired rate of delivery, as hereinafter described, and is, in turn, a function of e.g. patch size, pH of the carrier, etc.

The carrier preferably should have a pH of no higher than about eight or nine, although it can be made less basic or more acidic, as hereinafter described, in order to control nicotine penetration rates. Nicotine is well known to penetrate the intact skin, particularly at a pH of about seven or greater.

The amount of any agonist and any antagonist introduced into a liquid carrier is a function of the solubility of the components in the carrier as well as the desired rate of delivery. Moreover, patch construction to some extent will affect the rate of delivery.

The relative amounts of agonist and antagonist which are administered to a subject are functions their receptor occupancy. Thus, it is desirable to provide the relative amounts of agonist and antagonist which present an equivalent amount of binding at the brain receptors for the agonist.

It is also possible to add to the liquid carrier an agent to increase the permeability of the skin, such as dimethyl sulfoxide (DMSO) or equivalent agent. The dimethyl sulfoxide is a topical agent which facilitates penetration of the agonsit through the skin. Other similar acting agents which can be used include, e.g. sodium lauryl sulfate, 1-dodecyl-hexahydro-2H-azepin-2-one (Azone) and a mixture of propylene glycol and oleic acid.

The patch P has been found to be effective in administering either the antagonist or the agonist and preferably both in this embodiment of the invention. The patch is preferable inasmuch as it may provide a controlled rate of delivery of the agonist and antagonist to the user and also maintain a sustained level of the agonist and antagonist in the users bloodstream. By controlling the membrane size and like factors, it is possible to regulate the rate of delivery of these ingredients to the user. Moreover, the patch provides the desired pharmacologic effects to which the user is accustomed, but still blocks the need for the additional external administration of the drug. It also enables a disassociation of the convenient means for delivery of the drug. A person addicted to nicotine is accustomed to smoking as a means to derive that nicotine. When the patch is employed, there is no longer a reinforcement of the need for smoking to obtain the desired level of nicotine. In the case of a heroin addict who utilizes an intravenous needle, there is a disassociation in that the intravenous mode of administration is no longer required.

The second approach for treatment of drug dependencies utilizing the agonist and antagonist combinations relies upon an inverse conditioning for smoking cessation. This approach differs from the previously described approach in that the aim of the first approach is to saturate the nicotine receptors to thereby insulate the user from the reinforced effects of taking a drug. In this latter approach, the invention counter-conditions the stimuli associated with the administration of that drug by reversing the usual consequences of taking the drug.

In one of the preferred embodiments of the invention utilizing this latter approach of counter-conditioning, the drug or the agonist is applied to the individual in a level which would approximate that previously obtained by the individual. For example, the addict of heroin or morphine would receive methadone as the agonist to heroin or the morphine since methadone has a more constant systemic level. The methadone would be administered in amounts which would approximate the pharmacologic effects to which the individual was previously accustomed if the antagonist were not administered. In like manner, the party addicted to nicotine would receive that general level of nicotine to which he or she was previously accustomed. The administration of the nicotine or the other drug would preferably occur by any convenient means which was different than the addicted patients usual form of administration. Thus, the morphine or heroin could be taken through the oral cavity if the subject previously used intravenous delivery. The nicotine would preferably be applied by means of a transdermal patch. When a desired amount of the agonist has been assimilated into the system of the user, the user is then provided with a means for administration of the antagonist which would simulate the method previously used for taking the abused drug. In this case, for example, the user would be provided with naltrexone or otherwise naloxone in hypodermic needles, if in the past, the user had been accustomed to self-administering the morphine or heroin intravenously. Thus, the naltrexone would also be administered intravenously. It can be appreciated that when the user formerly administered a substance, he or she received a certain desired sensation. In this case, when the naltrexone is administered, there is an inverse conditioning in that there would be an unpleasant effect of withdrawal. The more that the user attempted to reinforce his or her habit by using intravenous needles, there would be a greater withdrawal. As a result, there is an inverse conditioning.

The same holds true in the case of the party addicted to nicotine. The act of smoking would then be negatively correlated with nicotine effects. The typical smoker is accustomed to receiving a nicotine reinforcement or so-called "high" by drawing puffs of smoke from a cigarette, a pipe, or other means for burning tobacco. In this case, the smoker is administered nicotine chronically through a transdermal patch or equivalent method of delivery other than by smoking. The smoker would also be provided with an artificial cigarette or other smoking device which contains mecamylamine as opposed to nicotine. In this case, the usual conditioning associated with smoking, namely increased nicotine stimulation and the pleasurable effects derived therefrom would not be obtained. In fact, there would be a withdrawal and in this paradigm, smoking would be associated with decreased nicotinic stimulation and the unpleasant effects of withdrawal. Thus, whenever the user smoked the artifical cigarette or similar smoking device, the user would be provided with the full range of sensory and motor aspects of smoking associated not with an increase, but rather a decrease in nicotine-induced satisfaction. The satisfaction provided by the systemic level of nicotine would be lessened by each bolus of mecamylamine that is inhaled.

FIGS. 6 and 7 clearly show this effect of inverse conditioning. By reference to FIG. 6, the normal nicotine receptor activation or satisfaction is shown on a scale as a function of time. Each puff of a cigarette or similar smoking device provides a certain level of satisfaction since each puff of the tobacco smoke provides the satisfying drug, nicotine. In the inverse conditioning as shown in FIG. 7, it can be observed that there is an elevated base line of nicotine in the subject's bloodstream. Thus, the subject is "pre-loaded" with nicotine from the transdermal patch. However, on each occasion when a puff of the artificial cigarette is taken, there is a decrease in the amount of the satisfaction obtained. Thus, in comparison, whereas an increase in satisfaction occurred with each puff, in FIG. 6, a decrease in the satisfaction results with each puff, as shown in FIG. 7.

Those artificial smoking devices which are illustrated and described in the aforementioned co-pending patent application (now U.S. Pat. No. 4,846,199) could be used for the purposes of administering the antagonist in accordance with this embodiment of the invention. One such smoking device is illustrated in FIG. 2 of the drawings and comprises an outer housing 20 which may adopt the size and shape of a conventional cigarette. Thus the housing 20 is elongate and cylindrically shaped. Located within the housing 20 is a concentrically disposed, diametrically reduced cylindrically shaped divider 22 which forms an ignitable fluid chamber 24 containing a suitable ignitable fluid, such as a conventional lighter fluid e.g. liquid propane, butane, or the like. Any conventional petroleum distillate, such as conventional lighter fluids, may be employed for this purposed.

A pair of intermediate discs or walls 26 and 28 are located within the housing 20. Concentrically disposed within the divider tube 22 is an elongate smoke delivery tube 30. Mounted on the right hand end of the smoke delivery tube 30, reference being made to FIG. 2 is a filter 32 to create a draw or inhalation resistance, such as in a conventional cigarette filter. Located at the opposite end of the smoke delivery tube 30 is an enlarged ampule or reservoir 34 containing the antagonist, mecamylamine. The ampule 34 may be formed of glass or graphite or other inert material.

Extending from the chamber 24 containing the ignitable fluid is a wick 36 having an end 38 capable of being ignited to create a flame. However, by reference to FIG. 2, it can be observed that the ampule 34 is located in a position where it is not immediately above the flame of the burnable end 38 and therefore is not heated. When the smoker desires to create an aerosol of the constituents in the ampule 34, the smoke delivery tube 30 and hence the ampule 34 are shifted to the left, reference being made to FIG. 2. The constituents in the ampule 34 will become heated and form an aerosol.

The ampule 34 may be provided with an air inlet opening 40 so that when a suction is imparted to the ampule 34, through the smoke delivery tube 30, the aerosol will travel through the smoke delivery tube 30 and through the filter 32. A similar opening 42 may be formed in the end wall of the housing 20 for this purpose. The air inlet opening 42 also operates as a vent to prevent excessive pressure build-up within the ampule 34.

Thus, when the smoker desires to inhale, an aerosolized amount of a charge of the mecamylamine will be generated and inhaled, providing the negative effects described above. The user merely pushes on the smoke delivery tube 30 so that the ampule 34 is located over the flame of the burnable end 38 and within a matter of a few seconds, a sufficient amount of aerosol has formed, equivalent to that which would be generated in a puff by the smoker on a normal cigarette. This aerosol could even be visually similar to normal cigarette smoke. It could also be incorporated with agents to provide a similar aroma and other sensory qualities resembling cigarette smoke.

A spring 44 is disposed between the right-hand end wall 26 in the outer housing 20 and the filter 32. Moreover, an outer cover sleeve 46 is disposed over the spring between the filter 32 and the housing 20. The housing 20, as well as the sleeve 46, may both be formed of a suitable paperboard material which is relatively inexpensive so that the entire apparatus functions as a disposable cigarette which may be disposed of when the charge of antagonist in the ampule 34 has been depleted. Otherwise, the entire apparatus of FIG. 2 could be constructed to be reusable with the ampule capable of being recharged.

It is possible to generate the aerosol at a relatively low temperature by boiling the liquid antagonist solution, namely mecamylamine solution. For example, temperatures as low as 200 degrees C. could be used for generating a vapor and hence an aerosol of the condensate. Consequently, there is no significant combustion and hence poisonous products of combustion. Alternatively, a nebulizer such as an ultrasonic nebulizer could be used to create the aerosol to thereby eliminate any heating of the contents of the ampule.

FIG. 3 illustrates a modified form of an apparatus for smoking of an antagonist, such as mecamylamine, and which comprises a conventional filter tipped cigarette 50 comprised of a paper tube 52 filled with ground tobacco 54. A conventional filter 56 is provided at the right-hand end of the cigarette in a conventional manner. The present invention provides an elongate tube 58 extending concentrically within the cigarette from one end thereof to the other and which is opened at each of the opposite ends. The tube 58 may also be formed of a paper material or similar burnable substance.

The tube 58 is provided on its interior with an antagonist such as mecamylamine. In this case, the antagonist could be in the form of a heavy gel which is coated on the interior surface of the tube 58. The burning cigarette 50 will provide the source of heat which will volatilize the mecamylamine. thus, as the left-hand end of the cigarette is ignited, the heat from the burning end of the cigarette will volatilize the mecamylamine enabling the mecamylamine to be inhaled by the smoker upon puffing at the filter 56.

In accordance with the construction illustrated in FIG. 3, it can be observed that there is very little draw resistance through the tube 58. Approximately 90 percent of any intake of the aerosol or smoke will be through the tube 58. While any drawing of air through the burning end of the cigarette will indeed produce cigarette smoke, this will be in a relatively small quantity. Nevertheless, this embodiment of the invention is effective in that it will provide some nicotine to the user so that there may not be a complete withdrawal syndrome. Thus, the device could be constructed so that the amount of nicotine which is generated can be proportioned to the amount of the antagonist, mecamylamine. In this way, it is possible to tailor the device to the particular needs of an individual in which smoking cessation is desired. This type of smoking apparatus is also effective in that it will have the feel and appearance of a conventional cigarette and will also enable the smoker to receive unaltered cigarette smoke along with the antagonist. If the amount of the antagonist is substantially greater than the amount of cigarette smoke, there still will be a net effect of a withdrawal. This further reinforces the decrease in nicotine-induced satisfaction.

FIGS. 4 and 5 illustrate another modified form of smoking device 60 and which is very similar in construction to the smoking device 50 of FIG. 3 in that it employs a conventional filter tip cigarette. In this embodiment, the elongate smoke delivery tube 58 is provided on its interior surface with a plurality of radially inwardly extending somewhat flexible fingers 62. These fingers may actually adopt the form of filaments and are sufficiently flexible so as to yield to the draw of aerosol through the delivery tube 58. The fingers 62 generally extend randomly throughout the annular interior surface of the delivery tube 58 and are effective to preclude any of the liquid antagonist from rolling out of the delivery tube 58 when the cigarette is held in a vertical position with the outer end located downwardly. Thus, the liquid antagonist will collect in the spaces 64 between the point of connection of the fingers 62 and the interior surface of the wall of the tube 58.

It can be observed that the smoking device 60 is also effective in generating an aerosol or smoke of the antagonist similar to the device in FIG. 3. Thus, this device would also be effective in increasing the negative effect associated with the smoking of a cigarette.

It can be observed in connection with this approach for reducing the dependence on drugs, and in particular nicotine, that there is an inverse conditioning to tobacco smoke whereby the act of smoking is negatively correlated with nicotine effects. The smoker is given nicotine through the patch or other means as aforesaid and the mecamylamine is obtained through an artificial cigarette which may simulate the appearance, size and shape of a conventional cigarette. As indicated above, this smoking would be associated with decreased nicotine stimulation and the unpleasant effects of withdrawal. As long as the subject did not resume tobacco smoking as through conventional cigarettes, this inverse conditioning would lessen the temptation provided by smoke from external sources, as for example from third parties cigarettes.

In the case of cocaine, amphetamines and other stimulants, an agonist such as bromocriptine could be used. The bromocriptine would typically be administered in an amount of about 40 to 100 milligrams per day. Again, this agonist could be taken orally or otherwise by means of a transdermal patch. However, with a transdermal patch, the bromocriptine agonist would typically be administered in a rate of about 10 to 25 milligrams per day. The antagonist for cocaine, amphetamines and these other stimulants would be fluphenazine such as fluphenazine hydrochloride. This fluphenazine hydrochloride would be taken at a rate of about 20 to 60 milligrams per day orally. In like manner, fluphenazine decanoate could also be used as an antagonist at a rate of about 25 to 75 milligrams in each three week period. This latter antagonist would be injected intramuscularly.

With respect to heroin and other opiates, the agonist is methadone and would normally be administered orally in an amount of about 30 to about 120 milligrams per day. The antagonist for the opiates is naltrexone, as aforesaid. The naltrexone would be administered in a rate of about 40 to about 70 milligrams per day. Again, the naltrexone could be administered orally or intravenously, although it is preferably administered intravenously to negatively correlate to the effects of the abused drug. It should be understood that other drug dependencies with drugs such as barbituates, benzodiazopines and alcohol could also be treated with this combination of agonist and antagonist treatment. Dangerous withdrawal symptoms would still be carefully monitored and controlled.

The invention is also effective in therapeutically treating psychophysiological diseases and disorders involving neuronal dysregulation and which may also involve a drug use. As indicated previously, psychiatric or neurologic disorders which involve the dysregulation of a neurotransmitter including manic depression and schizophrenia could be treated by the method of the present invention. In this case, for treatment of psychiatric dysorders of this type, bromocriptine would be used as an agonist, generally in the amounts used for treatment of cocaine. The fluphenazine, or other derivitives thereof, would be used as the antagonist, also in the ranges as indicated above.

Diseases involving the imbalances of the autonomic nervous system can also be treated by this agonist-antagonist drug administration. Sympathetic nervous system disorders, such as hypertension, could also be treated with administration of adrenergic agonists and antagonists. Parasympathetic nervous system disorders could also be treated with concurrent treatment of muscarinic cholonergic agonists and antagonists.

The present invention also provides a unique composition of the agonist and the antagonist as indicated above. This agonist and antagonist combination is effective and unique in that it would not be expected to provide the beneficial results described herein. One would assume that the agonist and antagonist would counter the effects of each other thereby providing essentially no effect whatsoever. However, it has been determined in accordance with the present invention that this combination of agonist and antagonist is highly beneficial as previously described. It is important to provide a composition to the user so that the user may not discard the antagonist and only resort back to the old habit of using the agonist. This is particularly true with the highly addictive drugs such as the opiates and the like. Thus, the composition of the invention is an important contribution to the practice of the method and is highly effective therefore.

EXAMPLES

The invention is further illustrated by but not limited to the following examples.

Example 1

Approximately three milligrams per hour of nicotine is administered to a subject having a nicotine dependency. The nicotine is administered by means of a transdermal patch applied to the forearm of the subject. Mecamylamine is also administered simultaneously through the same patch at a rate of 15 to 30 milligrams per day. It is found that this type of administration substantially occupies the receptors in the brain of the subject thereby reducing the desire for nicotine intake.

Example 2

In example 2 a subject having nicotine dependency is treated by administration of the agonist-antagonist combination in accordance with the present invention. In this case, the nicotine is administered to a subject through a transdermal patch such that there is about 20 nanograms of nicotine in each milliliter of the person's bloodstream at any point in time.

The subject is provided with a simulated cigarette or so-called artificial cigarette, similar to that illustrated in FIG. 3 of the drawings. The ampule of that artificial cigarette is provided with mecamylamine. When the user draws upon the filter of the cigarette, he receives a charge of mecamylamine which causes a withdrawal effect. This, in turn, inversely conditions the smoker and ultimately causes the smoker to associate negative feelings with smoking of cigarettes thereby reducing the tendency of the smoker to resort to a smoking habit.

Example 3

A subject having a heroin addiction is treated by cessation of all heroin administration. The subject is provided with about 70 milligrams per day of methadone and which is administered orally. Simultaneously, the subject is also provided with naltrexone administered at a rate of about 50 milligrams per day and which is administered orally.

The brain receptors for these opiates are substantially filled thereby reducing the desire of the subject for further intake of heroin or an agonist thereof.

Thus, there has been illustrated and described a unique and novel combination of an agonist and an antagonist for treatment of drug dependency and other psychophysiological diseases and disorders. The present invention thereby fulfills all of the objects and advantages which have been sought therefore. It should be understood that many changes, modifications, variations and other uses and applications will become apparent to those skilled in the art after considering this specification and the accompanying drawings. Therefore, any and all such changes, modifications, variations and other uses and applications which do not depart from the spirit and scope of the invention are deemed to be covered by the invention.

Having thus described our invention, what we desire to claim and secure by Letters Patent is:

1. A method of treating and reducing drug dependency on an abused drug whose addictive effects result at least in part from activation of nicotine receptors, said method comprising:

a) administering to a subject a nicotine receptor activating drug which causes nicotine receptors which are responsive to that activating drug to become activated and opened, said drug being present in an amount which would normally provide some of the desired pharmacologic effects provided by the abused drug to reduce the need or perceived need for the drug and to provide a sustained level of the nicotine receptor activating drug in the bloodstream of the user and at least partially saturate the nicotine receptors in the subject to whom the nicotine receptor activating drug is administered and which thereby satiates the need or perceived need for the abused drug by the subject, the nicotine receptor activating drug also being present in a sustained amount in the bloodstream of the user sufficient to result in a reduction of satisfaction of a need or perceived need for the abused drug obtained from the subsequent administration of the abused drug, and b) administering to the subject an antagonist to the nicotine receptor activating drug which blocks effects of the agonist which activates these receptors and which receptors are also sensitive to the antagonist, the antagonist being present in an amount sufficient to at least partially block the pharmacologic effects of the nicotine receptor activating drug while there is a substantial systemic amount of the nicotine receptor activating drug present, such that the administration of the nicotine receptor activating drug is complemented by the antagonist by occupying a greater number of receptors of the user of the nicotine receptor activating drug than would be occupied by the nicotine receptor activating drug alone and with a lesser number of receptors left available to respond to the abused drug, thereby insulating the user from the reinforcing effects of the abused drug, the nicotine receptor activating drug and the antagonist having opposing effects with regard to receptor stimulation but common effects with respect to attenuation of response to the abused drug due to receptor occupancy, at least the nicotine receptor activating drug having a delivery mode for delivering to the receptors of the user which is different from that previously employed with the abused drug.

2. The method of claim 1 further characterized in that the receptors for the nicotine receptor activating drug would be at least partially saturated by the nicotine receptor activating drug and the antagonist thereby reducing the desire for and dependency on the abused drug.

3. The method of claim 1 further characterized in that the nicotine receptor activating drug and the antagonist are administered simultaneously.

4. The method of claim 1 further characterized in that the nicotine receptor activating drug is administered initially and the antagonist is administered thereafter upon demand for the abused drug by the subject.

5. The method of claim 1 further characterized in that the nicotine receptor activating drug is administered in a reduced amount after a period of time.

6. The method of claim 1 further characterized in that the nicotine receptor activating drug and the antagonist are administered in an amount such that a substantial portion of the receptors which would otherwise be activated by the effects of the abused drug are saturated.

7. A method of pharmacologically treating and reducing drug dependency on an abused drug where the addictive effects depend on activation of nicotine receptors, said method comprising:
   a) administering to a subject a nicotine receptor activating drug which causes nicotine receptors which are responsive to the activating drug to become activated and opened and said drug being present in an amount which satisfies a demand for the abused drug and which reduces the need or perceived need for the drug, and
   b) simultaneously administering to the same subject an antagonist to the nicotine receptor activating drug and which receptors are also sensitive to the antagonist to thereby block the effect of the drug which causes activation of these receptors, the antagonist being present in an amount sufficient to attenuate the pharmacologic effects of the drug, the antagonist and the nicotine receptor activating drug in combination being present in an amount and regimen that more receptors for the nicotine receptor activating drug are occupied by the drug and the antagonist than would be occupied by the same regimen of the nicotine receptor activating drug alone and the antagonist alone and that a lesser number of receptors are left available to respond to subsequent doses of the abused drug thereby insulating the user from further reinforcing effects of the drug, and with the nicotine receptor activating drug and the antagonist having similar effects with regard to receptor occupancy, the nicotine receptor activating drug and the antagonist both being present in an amount such that toxic effects of the amount of the nicotine receptor activating drug and the toxic effects of the amount of the antagonist are attenuated by each other, at least the nicotine receptor activating drug having a delivery mode for delivering of the nicotine receptor activating drug or antagonist to receptors of the subject using the drug which is different from that previously employed with the abused drug.

8. The method of claim 7 further characterized in that the nicotine receptor activating drug may be present in an amount which would otherwise be toxic in the absence of the antagonist but which toxicity is offset by the presence of the antagonist.

9. The method of claim 7 characterized in that the nicotine receptor activating drug is administered in a sufficiently high dose to occupy a sufficient number of receptors to substantially reduce a subject's demand for the abused drug.

10. The method of claim 7 further characterized in that the nicotine receptor activating drug and the antagonist are administered by means of a transdermal patch.

11. The method of claim 7 further characterized in that the nicotine receptor activating drug is administered in a reduced amount after a period of time.

12. The method of claim 7 further characterized in that the nicotine receptor activating drug and the antagonist are administered in an amount such that a substantial portion of the receptors for the drug are saturated.

13. A method of treating and reducing drug dependency on a drug whose addictive effects depend at least in part on activation of nicotine receptors, said method comprising:
   a) administering to a subject a nicotine receptor activating drug which causes nicotine receptors which are responsive to the activating drug to become activated and opened, said drug being present in an amount which achieves the pharmacologic effects of the abused drug to which the subject was previously accustomed and reduces the need or perceived need of the abused drug,
   b) administering to the subject an antagonist to the nicotine receptor activating drug which blocks effects of an agonist which activates these receptors and which same receptors are also sensitive to the antagonist the antagonist also blocking the effect of the agonist, the agonist being administered in a manner to which the subject was previously accustomed to administration of the abused drug and also increasing the saturation of the receptors for the nicotine receptor activating drug by the antagonist and also causing a reduced systemic effect of the nicotine receptor activating drug, thereby reducing the satisfaction of the subject to the nicotine receptor activating drug and inversely conditioning the subject to the desire for the abused drug, at least the nicotine receptor activating drug being administered by a mode which is different from that previously employed for the abused drug.

14. The method of claim 13 further characterized in that the antagonist is administered by the subject.

15. The method of claim 13 further characterized in that the antagonist is administered by the subject under conditions which were present when previously administering the abused drug thereby counter-conditioning the stimuli associated with the abused drug.

16. The method of claim 13 further characterized in that the nicotine receptor activating drug is delivered from a transdermal patch and the antagonist is delivered from an inhalation device.

17. A pharmacologic composition for the treatment and reduction of dependency on an abused drug in which the addictive effects depend in part on activation of nicotine receptors, said composition comprising:
   a) the nicotine receptor activating drug, nicotine, which causes nicotine receptors which are responsive to that activating drug to become activated and opened, said nicotine being present in the composition in an amount which would provide a desired pharmacologic effect and at least partially satiate the needs or the perceived needs for the abused drug by a subject using the composition, and
   b) an antagonist to the nicotine receptor activating drug, mecamylamine, which is effective to block the effects of the nicotine which causes activation of these receptors and present in the composition in an amount sufficient to at least partially block the pharmacologic effects of the nicotine, the antagonist being selected so that the receptors which are responsive to the nicotine receptor activating drug are also sensitive to the antagonist, the relative amount of the nicotine and the relative amount of the mecamylamine being present in the composition so that there is a substantial systemic level of the mecamylamine present when there is a substantial systemic level of the nicotine present in the blood of a user of the composition, the nicotine and the mecamylamine being administered in the proper amounts and in a proper ratio to preclude intoxication or overdosing and to also reduce a derivation of pleasure of a subject when the abused drug is administered and to also prevent a state of withdrawal from the abused drug in the subject, such that the nicotine is complemented by the mecamylamine to occupy a greater number of receptors of the user of the nicotine than would be occupied by the nicotine alone and with the nicotine and the mecamylamine having opposing effects with regard to receptor stimulation but common effects with respect to attenuation of response to the abused drug due to receptor occupancy.

18. The composition of claim 17 further characterized in that the nicotine and the mecamylamine are administered contemporaneously.

19. A method of treating and reducing dependency on a drug whose addictive effects depend at least in part on activation of nicotine receptors, said method comprising:
   a) administering to a subject a nicotine receptor activating drug which causes nicotine receptors which are responsive to that activating drug to become activated and opened, said drug being present in an amount which would normally provide the desired pharmacologic effects of an abused drug and to reduce the need or perceived need for the drug used to provide a sustained level of the nicotine receptor activating drug in the bloodstream of the user and at least partially saturate the receptors of the subject for the nicotine receptor activating drug,
   b) administering to the subject an antagonist to the nicotine receptor activating drug which blocks effects of an agonist which activates these receptors and which receptors are also sensitive to the antagonist, the antagonist also being present in an amount sufficient to at least partially block the pharmacologic effects of the nicotine receptor activating drug while there is a substantial systemic amount of the nicotine receptor activating drug present, such that the administration of the nicotine receptor activating drug is complemented by the antagonist by occupying a greater number of receptors of the user of the nicotine receptor activating drug than would be occupied by the drug alone and with the drug and the antagonist having opposing effects with regard to receptor stimulation but common effects with respect to attenuation of response to the nicotine receptor activating drug due to receptor occupancy,
   c) the nicotine receptor activating drug and the antagonist being administered in the proper amounts and in a proper ratio to preclude intoxication and thereby reduce a derivation of additional pleasure from the abused drug by a subject to whom administered and to also prevent a state of withdrawal from the abused drug in the subject, and
   d) at least the nicotine receptor activating drug having a delivery mode for delivering of the nicotine receptor activating drug to receptors of the user which is different from that previously employed with the abused drug.

20. The method of claim 19 further characterized in that the nicotine receptor activating drug and the antagonist are administered simultaneously or substantially simultaneously so that little or no satisfaction is obtained from taking additional amounts of the abused drug since a substantial portion of the receptors which are activated by the abused drug are already occupied.

21. The method of claim 19 further characterized in that the nicotine receptor activating drug is administered initially and the antagonist is administered by the subject thereafter upon demand for the abused drug by the subject thereby conditioning the subject to a lack of pleasure associated with the abused drug.

22. A method of treating and reducing nicotine dependency, said method comprising:
   a) administering to a subject a nicotine receptor activating drug which causes nicotine receptors which are responsive to that activating drug to become activated and opened and said drug being present in an amount which achieves the pharmacologic effects which would be obtained by the subject from the same or other means of nicotine delivery, and which nicotine receptor activating drug thereby partially saturates the receptors of the subject for the nicotine and thereby provides substantially the same pharmacologic effects to which the subject is accustomed, the nicotine receptor activating drug being administered in an amount which satiates the need or perceived need for the nicotine by the subject, the nicotine receptor activating drug being present in a sustained amount in the bloodstream of the user and in such amount sufficient to result in a reduction of satisfaction of a need or perceived need for the nicotine upon self administration of the nicotine; and
   b) administering to the subject an antagonist to the nicotine receptor activating drug which blocks the effects of the drug which causes activation of these receptors and which receptors are also sensitive to the antagonist, the antagonist being present in an amount sufficient to at least partially block the pharmacologic effects of the nicotine receptor activating drug while there is a systemic amount of the drug in the subject's bloodstream, the nicotine receptor activating drug and the antagonist also being administered in the proper amounts and in a proper ratio to preclude intoxication and thereby reduce a derivation of any additional pleasure from the nicotine by a subject to whom administered and to also prevent a state of withdrawal from the nicotine in the subject, such that the administration of the nicotine receptor activating drug is complemented by the antagonist by occupying a greater number of receptors of the user of the nicotine receptor activating drug than would be occupied by the nicotine receptor activating drug alone and with the nicotine receptor activating drug and the antagonist having opposing effects with regard to receptor stimulation but common effects with respect to attenuation of response to the nicotine due to receptor occupancy, the nicotine receptor activating drug and the antagonist both being present in an amount such that toxic effects of the amount of the nicotine receptor activating drug and the toxic effects of the amount of the antagonist are attenuated by each other.

23. The method of claim 22 further characterized in that the nicotine receptor activating drug and the antagonist are administered simultaneously.

24. The method of claim 22 further characterized in that the nicotine receptor activating drug is administered initially and the antagonist is self-administered thereafter upon demand for nicotine by the subject.

25. The method of claim 24 further characterized in that the nicotine receptor activating drug is nicotine.

26. A method of therapeutically treating psychophysiological diseases and disorders resulting from neuronal dysregulation and reducing fluctuations in activation of nicotine responsive receptors which would mediate neuronal dysregulation, said method comprising simultaneously administering to a subject a first component comprised of a drug or an agonist of the drug, and a second component comprised of an antagonist to the drug or agonist, the first component being administered in an amount which would tend to reduce the psychophysiological disease or disorder resulting from underactivity of the nicotine responsive receptors, the second component being administered in an amount which tends to reduce the psychophysiological disease or disorder resulting from overactivity of the receptors, both the drug or agonist and the antagonist being co-administered in an amount to reduce the systemic effects of the two components and which in combination counters the effects of the psychophysiological disease or disorder and reduces fluctuations in the nicotine responsive receptor actuation caused by generation of an endogenous substance of a subject, the first and second components each being present in substantial systemic amounts.

27. The method of claim 26 further characterized in that the drug or its agonist is administered in a reduced amount after a period of time of using the method and achieving selected results therefrom.

28. The method of claim 26 further characterized in that the drug or its agonist and the antagonist are administered in an amount such that a substantial portion of the receptors for the drug are saturated.

29. A pharmacologic composition for the treatment and reduction of drug dependency and psychophysiologic disorder and diseases in a subject, and reducing fluctuations in activation of nicotine responsive receptors mediating a drug dependency and where the drug activates nicotine responsive receptors, said composition comprising:

a) nicotine present in the composition in an amount which would cause the nicotine receptors of the subject responsive to that drug or agonist to become activated and provide a desired pharmacologic effect and at least partially satiate the needs or perceived needs for the drug by the subject using the composition, and b) an antagonist mecamylamine to nicotine present in the composition in an amount sufficient to at least partially block the pharmacologic effects of the nicotine which activates these nicotine responsive receptors and thereby reduce the systemic effects of the nicotine, the amount of the nicotine and the amount of the mecamylamine being present in the composition so that there is always a substantial systemic level of the mecamylamine present when there is a substantial systemic level of the nicotine present in the blood of a subject using the composition, the nicotine and the mecamylamine being present in the composition to be administered in the amounts and in a ratio to preclude intoxication and to also reduce a derivation of any pleasure of a subject to whom administered and to also prevent a state of withdrawal from the nicotine in the subject having a drug dependency to thereby reduce fluctuations in addiction mediating nicotine responsive receptor activation caused by administration of nicotine or withdrawal from the nicotine, the nicotine causing the nicotine responsive receptors of the receptor containing cells to be activated and the mecamylamine causing nicotine responsive receptors of the same cells to be blocked, the amount of the nicotine and the mecamylamine also be established so that the nicotine is complemented by the mecamylamine to occupy a number of addiction mediating receptors of the subject using the nicotine which is greater than the number of nicotine responsive receptors which would be occupied by the nicotine alone and with the nicotine and the mecamylamine having opposing effects with regard to receptor stimulation but common effects with respect to attenuation of response to the nicotine due to receptor occupancy, at least nicotine being provided in a form so as to be administered by a technique other than that to which the user was accustomed to administering the drug.

30. The composition of claim 29 further characterized in that the nicotine and the mecamylamine are administered simultaneously.

31. A method of therapeutically treating physiological dysfunction resulting from dysregulation in which the activity of a nicotine responsive receptor system is fluctuating and reducing fluctuations in activation of nicotine responsive receptors mediated by an endogenous substance in a subject having such dysregulation, said method comprising simultaneously administering to a subject a composition comprised of a first component comprised of a drug or an agonist of the drug which activates nicotine responsive receptors of the subject and a second component comprised of an antagonist to the drug or agonist, the first component being administered in an amount which would tend to improve the physiological disease or disorder resulting from under activity of said receptor system by increasing the activity of the nicotine responsive receptor system, the second component being administered in an amount which tends to improve the physiological disease or disorder resulting from overactivity of said nicotine responsive receptor system by decreasing activity of the receptor system, both the drug or agonist and the antagonist being administered in an amount to reduce the systemic effects of the other component and which in combination counters the effects of the physiological disease or disorder and reduces fluctuations in nicotine responsive receptor activation caused by the endogenous substance, the first and second components each being present in substantial systemic amounts and with the drug or agonist causing the nicotine responsive receptors of receptor containing cells to be activated and the antagonist causing nicotine responsive receptors of the same cells to be blocked.

32. The method of claim 31 further characterized in that the drug or agonist and the antagonist is administered in a reduced amount after a period of time of using the method and achieving selected results therefrom.

33. The method of claim 31 further characterized in that the drug or agonist and the antagonist is administered in a reduced amount after a period of time of using the method and achieving selected results therefrom.

34. The method of claim 31 further characterized in that the drug or agonist and the antagonist are administered in an amount such that a substantial portion of the receptors for the drug are saturated.

35. A method of therapeutically treating fluctuations of a physiological body activity of a subject which results from fluctuations of a nicotine responsive receptor system of the subject with respect to a certain desired level and where the nicotine responsive receptors of that system are activated by an endogenous substance of the subject, and where fluctuations in the endogenous body substance produce the fluctuations in the nicotine responsive receptor activation of that receptor system; said method comprising simultaneously administered to the subject a composition comprised of a first component comprising a drug or an agonist of the drug which if administered in absence of an antagonist to the drug would cause a substantial increase of the physiological activity and a second component comprised of an antagonist which if administered in absence of the drug or agonist would cause a substantial decrease in the physiological activity with respect to the desired level, the amount of the agonist and antagonist present being established so that a substantial portion of the nicotine responsive receptors of that receptor system are occupied by the agonist and antagonist sufficient to reduce fluctuations of the nicotine responsive receptor system caused by the fluctuations in the endogenous substance and with the drug or agonist causing nicotine responsive receptors of receptor containing cells to be activated and the antagonist causing nicotine responsive receptors of the same cells to be blocked to produce a desired level of nicotine responsive receptor activity.

36. The method of claim 35 further characterized in that said certain desired level is a normal body level with respect to fluctuations of the receptor system.

37. The method of claim 35 further characterized in that said method comprises administering the composition so that the receptor system has a substantial amount of the receptors saturated with the agonist and antagonist until the physiologic activities of the subject which result from the receptor system fluctuation are substantially attenuated.

38. A pharmacologic composition for the treatment of physiologic dysfunction of a subject in which the activity of a nicotine responsive receptor system is fluctuating and where the composition reduces those fluctuations, said composition comprising nicotine present in the composition in an amount which would prevent under-activity of the nicotine responsive receptor system causing the psychologic dysfunction and where the nicotine responsive receptor system is responsive to nicotine, and mecamylamine, an antagonist to the nicotine present in the composition and where the nicotine responsive receptor system is sensitive to the mecamylamine and being present in an amount sufficient to prevent over-activity of the nicotine responsive receptor system and at least partially block the pharmacologic effects of the nicotine and thereby reduce the systemic effects of the nicotine, and also reduce fluctuations in the activity of nicotine responsive receptors of that nicotine responsive receptor system, the amount of the nicotine and the amount of the mecamylamine being present in the composition so that there is always a substantial systemic level of the mecamylamine present when there is a substantial systemic level of the nicotine present in the blood of a user of the composition, the nicotine and the mecamylamine being administered in amounts and in a ratio to preclude intoxication and to also prevent under-activity of a receptor system causing the physiologic dysfunction, such that the nicotine is complemented by the mecamylamine to occupy a number of receptors of the subject using the nicotine which is greater than the number of receptors which would be occupied by the nicotine alone, and with the nicotine causing the nicotine responsive receptors of receptor containing cells to be activated and the mecamylamine causing nicotine responsive receptors of the same cells to be blocked and the mecamylamine having opposing effects with regard to the nicotine with regard to receptor stimulation but common effects with respect to receptor occupancy.

39. The composition of claim 37 further characterized in that the nicotine and the mecamylamine are administered simultaneously.

40. A composition for therapeutically treating physiological body activities of a subject which results from fluctuation of a nicotine responsive receptor system of the subject with respect to a certain desired level and where fluctuations in amounts of an endogenous body substance of the subject produce fluctuations in the activity of the nicotine responsive receptors of that nicotine responsive receptor system; said composition comprising a first component comprising nicotine which if administered in absence of an antagonist to the nicotine would cause a substantial increase of physiological activity of the subject and a second component comprised of an antagonist, mecamylamine which if administered in absence of the nicotine, would cause a substantial decrease in the physiological activity with respect to the desired level, the amounts of the nicotine and mecamylamine sufficient to reduce the fluctuations of the receptor system to a range close to the desired level and with the nicotine causing nicotine responsive receptors of receptor containing cells to be activated and the mecamylamine causing nicotine responsive receptors of the same cells to be blocked, and the nicotine and the mecamylamine being packaged for generally simultaneous administration to the subject.

41. The composition of claim 39 further characterized in that the nicotine is present in the composition in an amount so that the nicotine responsive receptor system has a substantial amount of the receptors saturated with the nicotine, and the mecamylamine also being present in an amount so that the fluctuations of physiological activities of the subject which result from fluctuations in activation of the nicotine responsive system is substantially attenuated.

* * * * *